United States Patent
Lepage et al.

(10) Patent No.: US 8,049,494 B2
(45) Date of Patent: Nov. 1, 2011

(54) FLEXIBLE ARRAY PROBE FOR THE INSPECTION OF A CONTOURED SURFACE WITH VARYING CROSS-SECTIONAL GEOMETRY

(75) Inventors: Benoit Lepage, Québec (CA); Martin Roy, Québec (CA); Stefano Orsi, Levis (CA)

(73) Assignee: Olympus NDT, Waltham, MA (US)

( * ) Notice: Subject to any disclaimer, the term of this patent is extended or adjusted under 35 U.S.C. 154(b) by 813 days.

(21) Appl. No.: 12/123,834

(22) Filed: May 20, 2008

(65) Prior Publication Data
US 2008/0315871 A1    Dec. 25, 2008

Related U.S. Application Data

(60) Provisional application No. 60/939,171, filed on May 21, 2007.

(51) Int. Cl.
*G01N 27/82* (2006.01)
*G01N 27/90* (2006.01)

(52) U.S. Cl. ......... 324/222; 324/228; 324/238; 324/244

(58) Field of Classification Search .................. 324/222, 324/228, 238, 244
See application file for complete search history.

(56) References Cited

U.S. PATENT DOCUMENTS
4,543,528 A    9/1985   Baraona

OTHER PUBLICATIONS

Office Action issued by the Chinese Patent Office on Aug. 5, 2010 in connection with corresponding Chinese Patent Application No. 200810127736.X.
English translation of Chinese Office Action issued in connection with Chinese Patent Application No. 200810127736.X on Aug. 5, 2010.

*Primary Examiner* — Reena Aurora
(74) *Attorney, Agent, or Firm* — Ostrolenk Faber LLP

(57) ABSTRACT

A flexible array probe is disclosed suitable for use in the non-destructive testing and inspection of test pieces with varying cross-sectional geometries. Array elements—such as, but not limited to, eddy current sensors, piezoelectric sensor elements, and magnetic flux leakage sensors—are mounted on thin alignment fins and coupled together with pairs of pivot mechanisms along the axis of desired rotation. The pivot mechanisms allow rotation in exactly one dimension and force the flexible array probe to align its elements orthogonally to the surface of the structure under test. Alignment and coupling fixtures are also disclosed.

37 Claims, 14 Drawing Sheets

FLEXIBLE ARRAY PROBE FOR THE INSPECTION OF A CONTOURED SURFACE WITH VARYING CROSS-SECTIONAL GEOMETRY

CROSS-REFERENCE TO RELATED APPLICATIONS

This application claims the benefit and priority of U.S. Provisional patent application Ser. No. 60/939,171 filed on May 21, 2007 entitled FLEXIBLE ARRAY PROBE FOR THE INSPECTION OF A CONTOURED SURFACE WITH VARYING CROSS-SECTIONAL GEOMETRY, the entire disclosure of which is included herein by reference.

BACKGROUND OF THE INVENTION

The present invention relates to array probes for non-destructive testing and inspection, and more particularly, to a flexibly eddy current or ultrasonic array probe assembly which can be applied and used to inspect contoured surfaces of varying cross-sectional geometry.

Any discussion of the related art throughout this specification should in no way be considered as an admission that such art is widely known or forms part of the common general knowledge in the field.

Although much of the discussion in the present disclosure speaks specifically to eddy current array probes, it is not limited in this regard. The flexible array probe of the present invention is well suited to any surface coupling array probe, such as, but not limited to, eddy current sensors, piezoelectric sensor elements—such as, but not limited to, ultrasonic transducers and bond testing probe elements—and magnetic flux leakage sensors—such as, but not limited to, Hall Effect sensor elements—devices.

Eddy current inspection is commonly used to detect flaws in manufactured components, such as tubes or billets. An inspection coil, typically referred to as an eddy current probe, is positioned near a piece to be inspected and driven with high frequency alternating electrical currents which, in turn, create an alternating magnetic field near the surface of the test piece. This magnetic field induces eddy currents in the conductive surface of the test piece which are sensed and measured by the eddy current probe. If a flaw or defect is present on the surface of the test piece, the flow of eddy currents will be altered, and this change will be readily detected by the eddy current probe. The amplitude and position of these current changes can then be analyzed and recorded, for example through visual inspection by a test operator or processed through an automated alarm algorithm, to determine the size and location of the defect or flaw. Eddy current array systems comprise of a plurality of inspection coils (or other types of eddy current sensors well known to those skilled in the art) arranged in such a way as to be conducive to a particular inspection task.

Eddy current inspection of contoured surfaces has long been a challenge in non-destructive testing and inspection. Some manufacturing processes—for example, billet rolling systems—can produce items with cross-sectional geometries defined only within a certain tolerance range. This variation on the shape of the test surface can make certain key aspects of eddy current inspection problematic. Maintaining a constant liftoff—the height at which an eddy current sensor is positioned above a test surface—for example can become extremely difficult using a solid, inflexible eddy current array probe. Similarly, it is critical that the axis of each eddy current sensor be held orthogonal to the surface under test. Using an eddy current array probe which holds its elements in fixed positions, this can be impossible to achieve while testing parts with varying geometry.

U.S. Pat. No. 4,543,528 to Baraona describes a flexible probe assembly which attempts to address these problems. Baraona's array probe uses a plurality of independent test heads—each housing at least one array element—fixed to each other with flexible bands. A two point coupling and alignment fixture—referred to as an "urging mechanism"—is also provided.

While Baraona's flexible array probe provides a reasonable solution to the problem of inspecting a convex surface, it holds a number of limitations. The range of motion (rotation) of each element in the array is limited by the rigidity of the flexible bands and by the spacing of the test heads. To achieve a useful probe curvature, array elements must either be spaced a distance apart or multiple elements placed on each test head. Both options significantly limit the usefulness of the flexible array probe. Baraona's probe and alignment fixture also make a poor showing of maintaining orthogonal coil orientation along sharply curved surfaces. Due to the nature of the design, each test head is allowed a degree of mobility against those directly adjacent to it, and the two point alignment fixture is not suited to support or align the critical center array elements. Furthermore, the design as presented is only suitable for testing convex surfaces.

Accordingly it would be advantageous to provide a robust flexible array probe which provides a large degree of flexibility while maintaining a tight element arrangement. Further, it would also be advantageous if the flexible array probe inherently tended to align its elements orthogonally to the surface of a structure under test. It would also be advantageous if the flexible array probe were conducive to measuring test pieces with variations in their cross-sectional geometry while maintaining a consistent eddy current sensor liftoff and orientation for every element in the array. It would further be advantageous if the probe were conducive to coupling to multiple curve shapes, including, but not limited to, convex, concave, and S-shaped surfaces.

SUMMARY OF THE DISCLOSURE

It is the object of the present disclosure to overcome the problems associated with prior art. The present disclosure does this by introducing a novel flexible array probe comprising thin array element mounting fins coupled together by pairs of pivot mechanisms located along the desired axis of rotation. The pivot mechanism pairs allow the elements of the array to rotate in exactly one dimension, while preserving a tight element arrangement and inherently aligning the elements orthogonally with the surface of the structure under test. In this way, the resulting flexible array probe will be pliant enough to respond to variations in the cross-sectional geometry of a structure under test—such as, but not limited to, variations directly relating to the manufacturing process of the structure under test—without the need for any mechanical adjustment.

Accordingly it is the object of the present disclosure to provide a robust flexible array probe built with pivot mechanisms which allow a large degree of flexibility while maintaining a tight probe element arrangement.

It is also an object of the present disclosure that the flexible array probe inherently, through use of the pivot mechanisms, align its elements orthogonally to the surface of a structure under test.

It is further an object of the present disclosure that the flexible array probe be conducive to measuring test pieces with variations in their cross-sectional geometry while maintaining a consistent probe element liftoff and orientation for every element in the array.

It is further an object of the present disclosure that the probe be conducive to coupling to multiple curve shapes, including, but not limited to, convex, concave, and S-shaped.

It is further an object of the present disclosure to provide a method and fixture of the alignment and coupling of the flexible array probe.

Other features and advantages of the present invention will become apparent from the following description of the invention which is provided below in relation to the accompanying drawings.

DETAILED DESCRIPTION

The present disclosure describes a flexible eddy current array probe comprising a plurality of thin array element mounting fins (referred to herein as "probe fins") coupled together with sets of pivot mechanisms thereby allowing probe elements fixed to the probe fins to rotate in exactly one dimension. In this way, a flexible array probe of any size and shape can be realized. The details of the different types of pivot mechanisms used and the construction of the flexible array probe are discussed in detail below.

Although the present disclosure speaks specifically to an eddy current array probe, it is not limited in this regard. Indeed, the devices and methods of the present disclosure are well suited to any surface coupling array probe, such as, but not limited to, eddy current sensors, piezoelectric sensor elements, and magnetic flux leakage sensors devices.

Figure 1A:
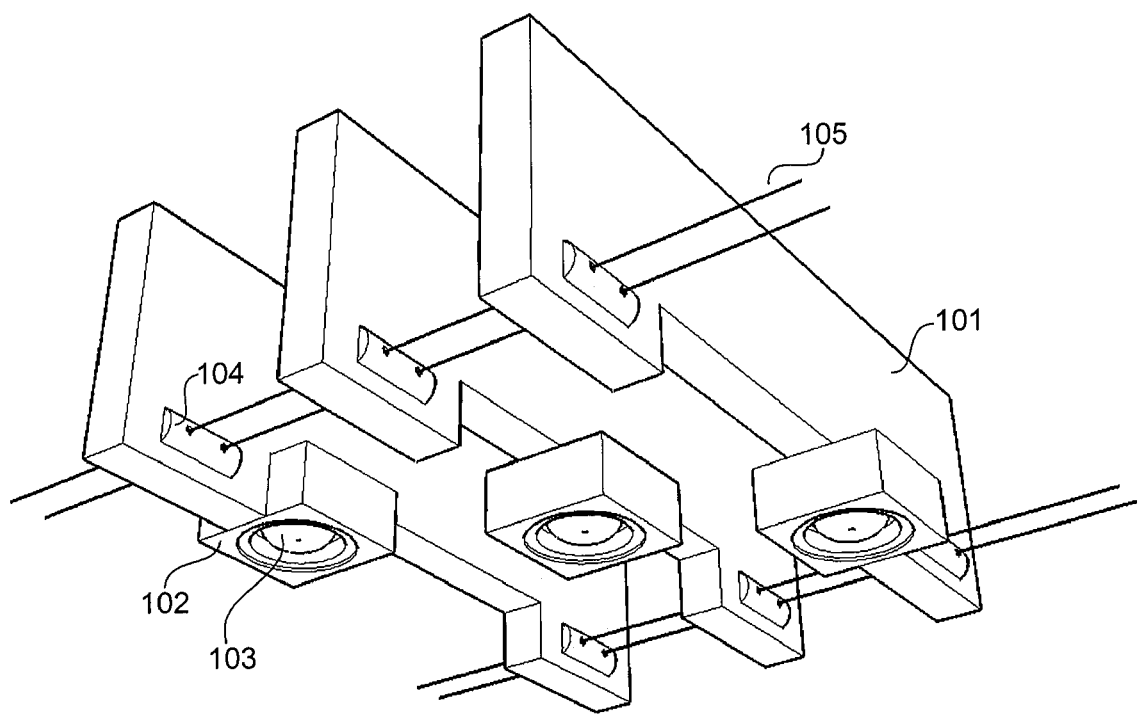
FIGS. 1A-1B are perspective drawings illustrating the assembly of the flexible array probe of the present disclosure using the cylindrical tab/slot pivot mechanism.
Figure 1B:
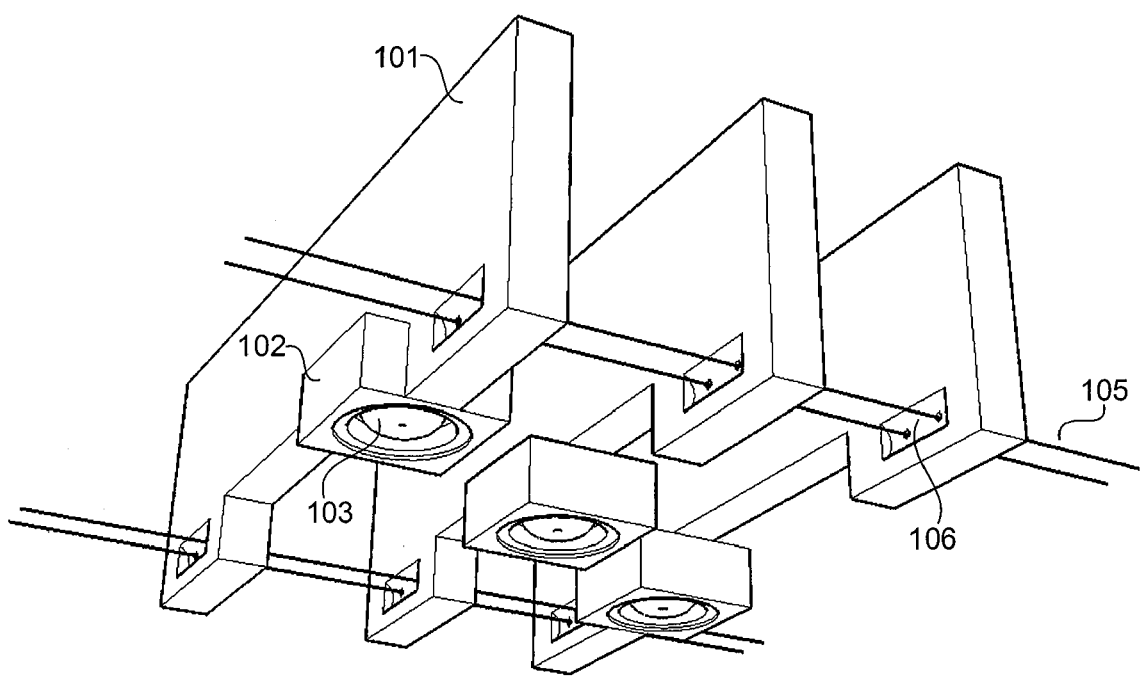

FIGS. 1A and 1B illustrate the assembly of the preferred embodiment of the present disclosure. Both figures are intended to show the same assembly process from different angles. Probe fins 101 are fixed with probe element housings 102 in appropriate locations, contingent on the size and shape of the array required. Depending on the material used and construction method, the probe fins 101 and the probe element housings 102 may be built as one solid piece. In the exemplary flexible array probe depicted in FIGS. 1A and 1B, eddy current sensor elements 103 are secured in the probe element housings 102.

Cylindrical tabs 104 and matching cylindrical slots 106 are molded on or machined into probe fins 101. Holes are drilled through each slot/tab pair, and wire 105 is drawn through. In a later assembly step (illustrated in FIG. 5 and discussed in detail below), the probe fins 101 are pulled together, and the wires 105 pulled to the desired tension, trimmed, and sealed against the outermost probe fins 101.

A preferred embodiment, as illustrated in FIGS. 1A and 1B, shows a pair of holes drilled through each slot/tab pair and consequently a pair of wires 105 running through each slot/tab pair. However, the disclosure is not limited in this regard. More or fewer holes and wires may be used depending on the degree of flexibility or stiffness required for an application. It should also be noted that while cylindrical tabs 104 and corresponding cylindrical slots 105 are used in the exemplary flexible array probe depicted in FIGS. 1A and 1B, the present disclosure is not limited in this regard. Indeed, tab and corresponding slot elements can take a plurality of geometric shapes, including, but not limited to, spherical.

Figure 2A:
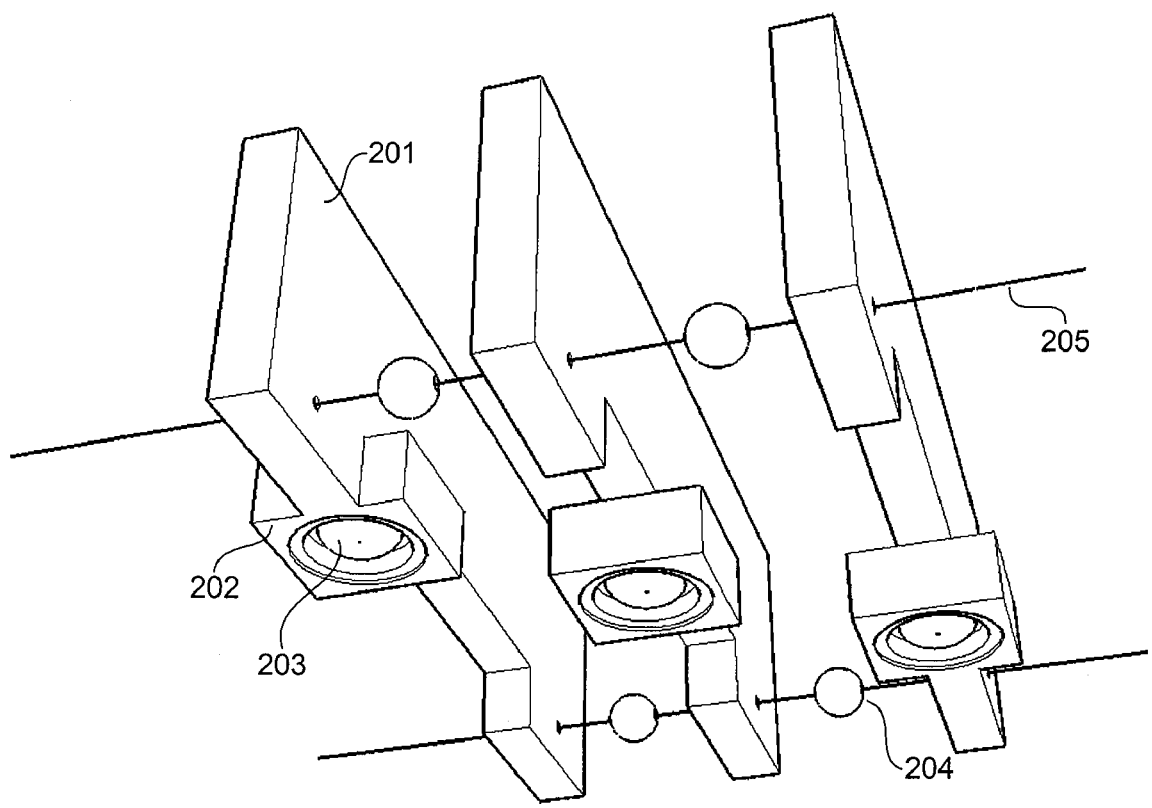
FIG. 2A is a perspective drawing illustrating the assembly of the flexible array probe of the present disclosure using the spacer element pivot mechanism.
Figure 2B:
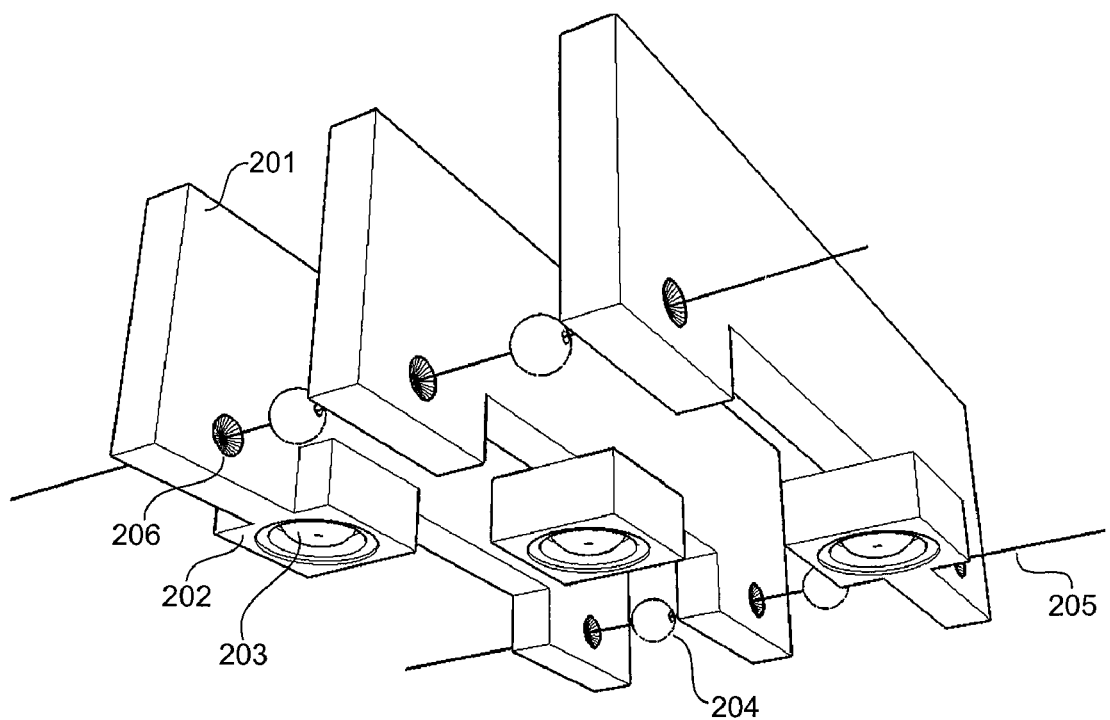
FIG. 2B is a perspective drawing illustrating the assembly of the flexible array probe of the present disclosure using the spacer element pivot mechanism along with space element alignment slots.

FIG. 2A illustrates an alternate embodiment of the present disclosure. The design is identical to the preferred embodiment except that the cylindrical slots 106 and tabs 104 of FIGS. 1A and 1B are replaced with spacer elements 204. These spacer elements 204 can be made of any material suitable to the application—for example, but not limited to, copper, plastic, rubber, or carbide as well as self lubricating materials such as Polyetheretherketone (commonly termed PEEK in the industry) and Acetal—and can be sized to provide a significantly larger range of element spacing that the cylindrical slot/tab pivot mechanism of the preferred embodiment can allow. While the spacer elements 204 depicted in FIG. 2 are spherical, the methods of the present disclosure are not limited in this regard. Spacer elements 204 can take a plurality of geometric shapes, such as, but not limited to, cylindrical, square, and trapezoidal. FIG. 2B represents an alternate embodiment of the present disclosure wherein spacer element alignment slots 206 are provided on the surface of the probe fins 201, providing an alignment means for spacer elements 204. Such an alternative embodiment is well suited for use with spacer elements 204 made from a rigid material, such as, but not limited to, plastic or copper.

Figure 3:
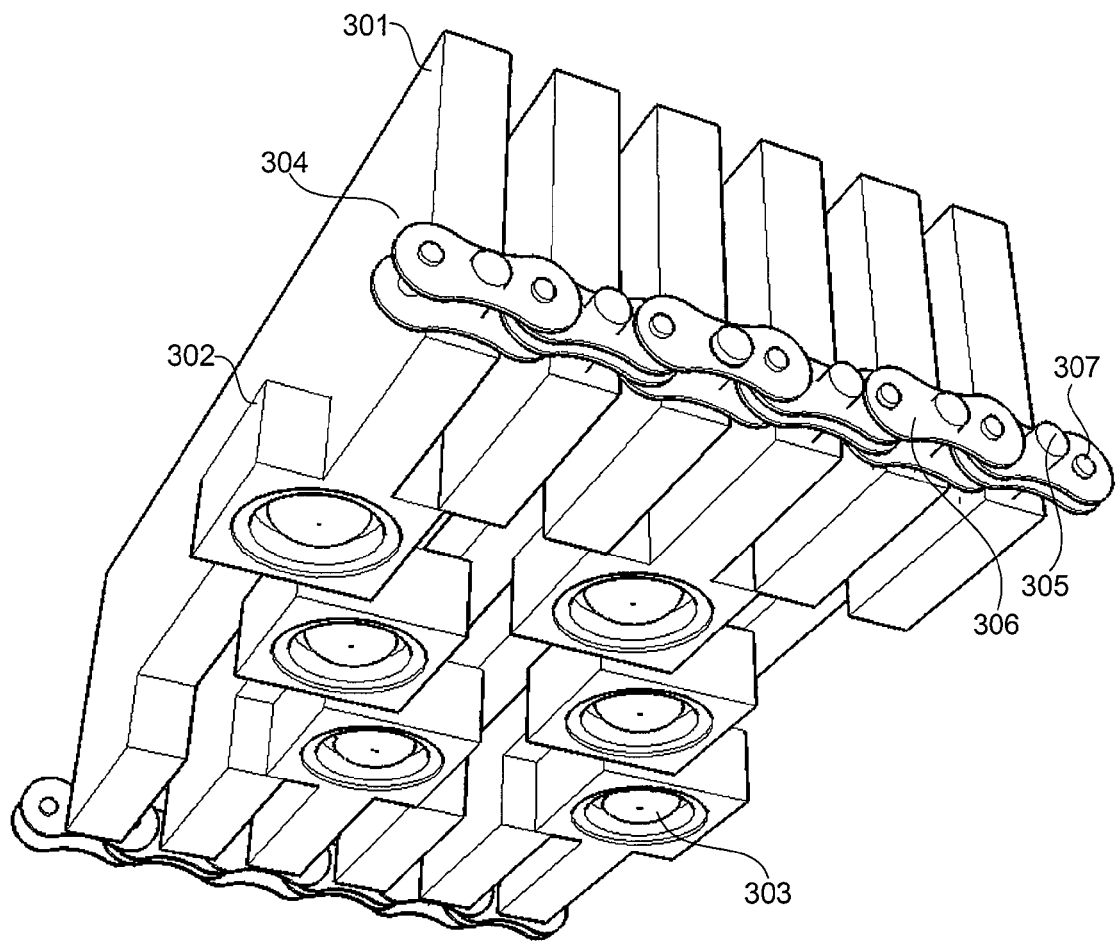
FIG. 3 is a perspective drawing illustrating the assembly of the flexible array probe of the present disclosure using the chain pivot mechanism.

FIG. 3 illustrates another alternate embodiment of the present disclosure. In this embodiment, the probe fins 301 are fixed with mounting posts 305 along the desired axis of rotation, and fixed to link elements 306. The link elements 306 are then coupled together with posts 307 to form a chain assembly 304. In this embodiment, a pair of these chain assemblies 304 is used; one along each side of the array assembly. This embodiment provides a very robust flexible array probe and can be used to create a flexible array probe which retains its shape after manipulation—two features which can be of great benefit to a manual inspection processes.

It should be noted that while the exemplary flexible array probe illustrated in FIG. 3 depicts mounting posts 305 securing probe fins 301 to link elements 306, the present disclosure is not limited in this regard. Indeed, a plurality of securement methods can be used to affix said link elements 306 to said probe fins 301, including, but not limited to, epoxy, mounting screws, and multiple support post systems, so long as the individual link elements 306 are not permitted to rotate with respect to the individual probe fins to which they are secured.

Figure 4:
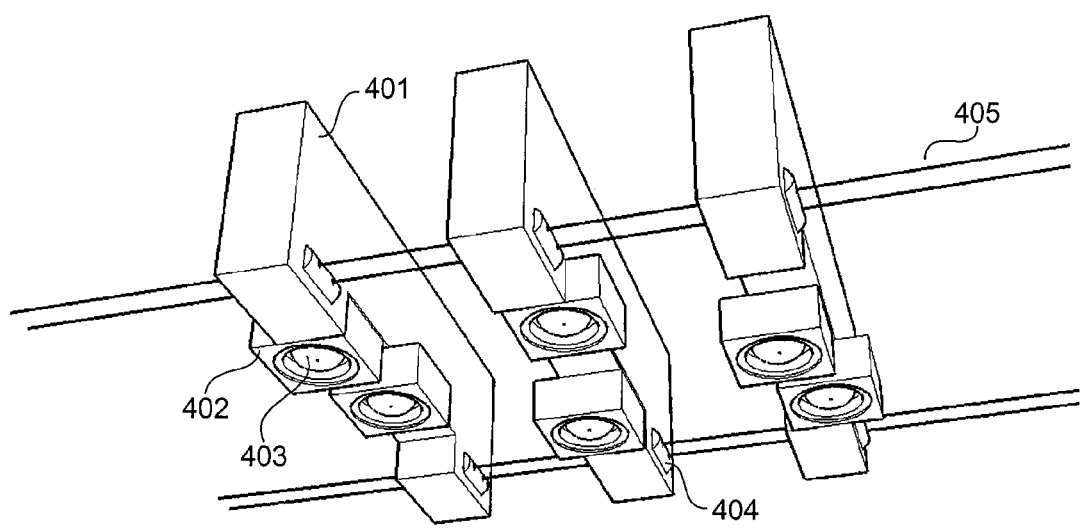
FIG. 4 is a perspective drawing illustrating an alternate embodiment of the flexible array probe of the present disclosure which makes use of multiple probe element housings per probe fin.

FIG. 4 illustrates a third alternate embodiment wherein each of the probe fins 401 is fixed with multiple probe element housings 402 and consequently probe elements 403. FIG. 4 depicts the cylindrical tab/slot pivot mechanism as used in the preferred embodiment, but this embodiment is not limited in this regard. Indeed, any of the three pivot mechanisms (cylindrical slot/tab, spacer ball, or chain) can be used with this multiple probe element housing technique.

Figure 5:
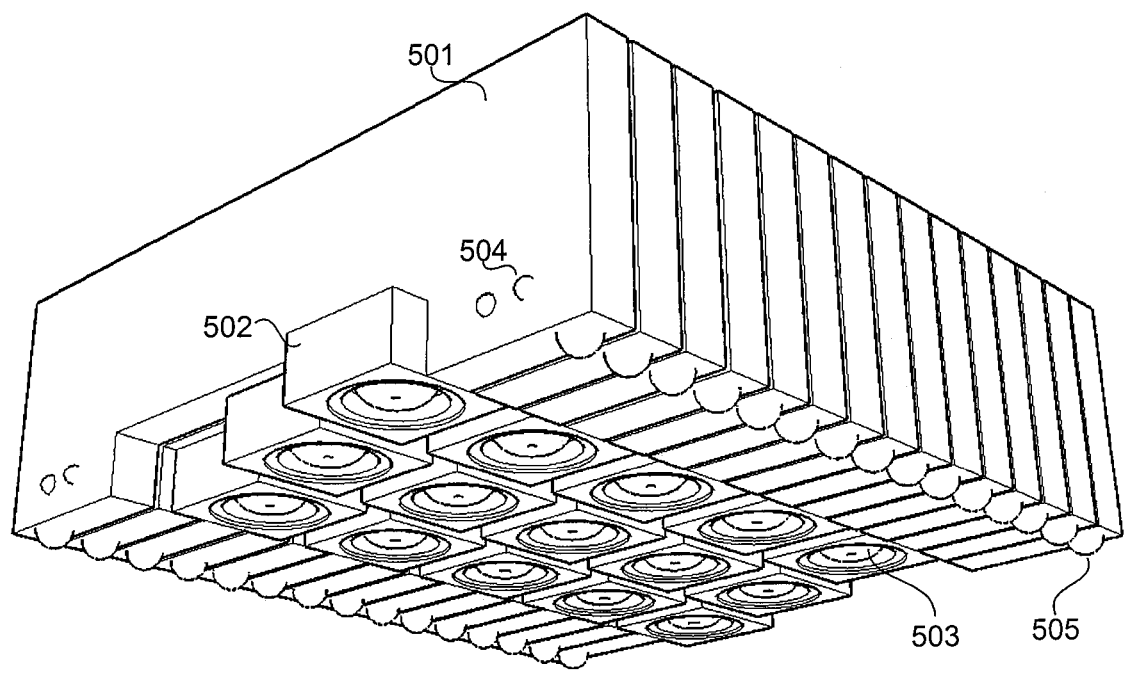
FIG. 5 is a perspective drawing illustrating the completely assembled flexible array probe of the present disclosure.

FIG. 5 illustrates a completely assembled flexible array probe built using the preferred embodiment of the present disclosure. A plurality of probe fins 501 are brought together using the tab/slot pivot mechanism illustrated in FIG. 1 and held together using the sets of wires also show there. For the final product the wires are pulled to the desired tension, trimmed, and then fixed in place using epoxy 504. While epoxy 504 is depicted in this and subsequent figures, other methods of securement may be used, including, but not limited to, clamps, clips, mounting screws, and stop sleeves. Wear shoes 505 made from a hard, low friction material such as, but not limited to carbide, may be added to the mating surface of the flexible array probe to protect and extend the life of the probe.

Within this assembly, the probe element housings 502 are brought together into a tight array, flexible in exactly one dimension. It should be noted that while the exemplary probe shown in FIG. 5 (and used in many of the other figures) is a 3×5 array probe, an array probe of any dimension can be realized using the methods of the present disclosure.

Figure 6:
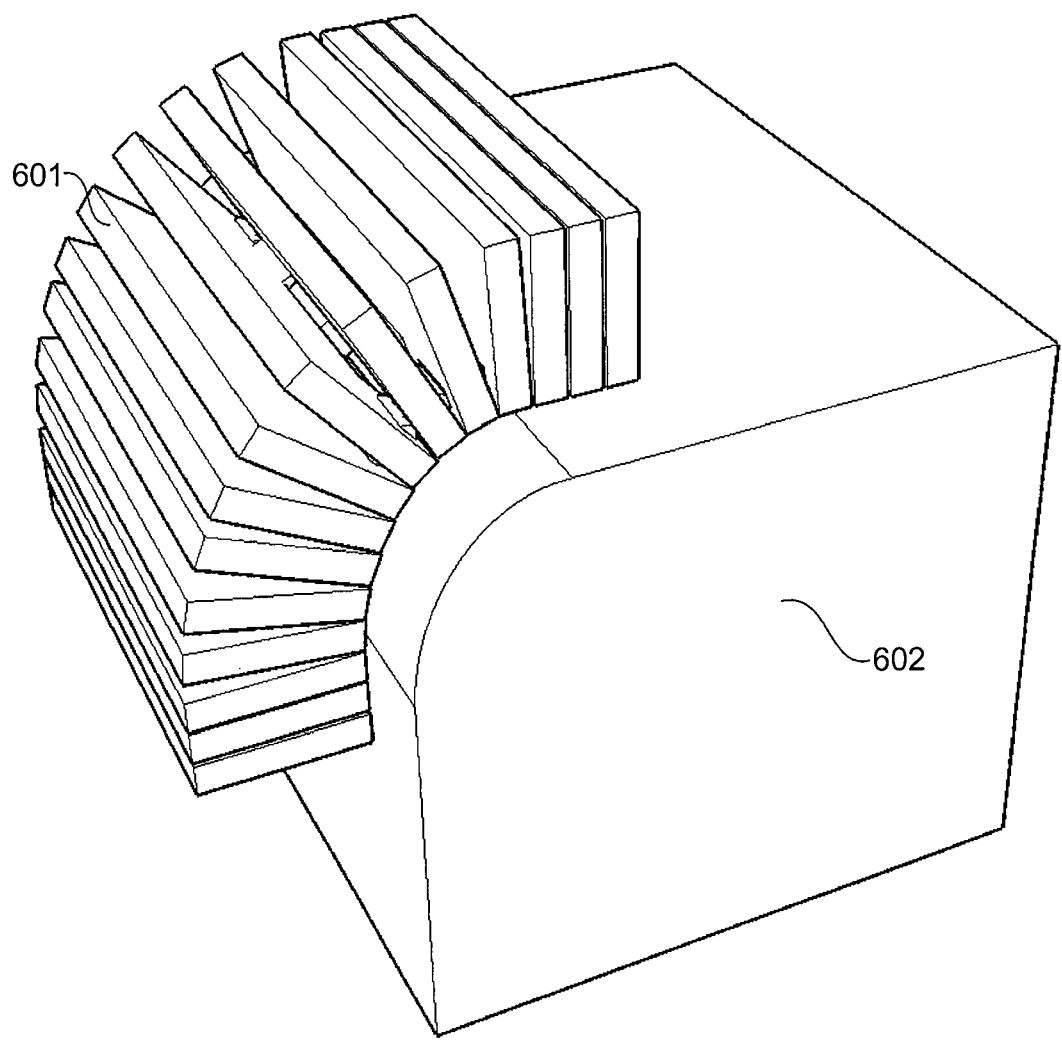
FIG. 6 is a perspective drawing illustrating the flexible array probe of the present disclosure being applied to a convex surface.
Figure 7:
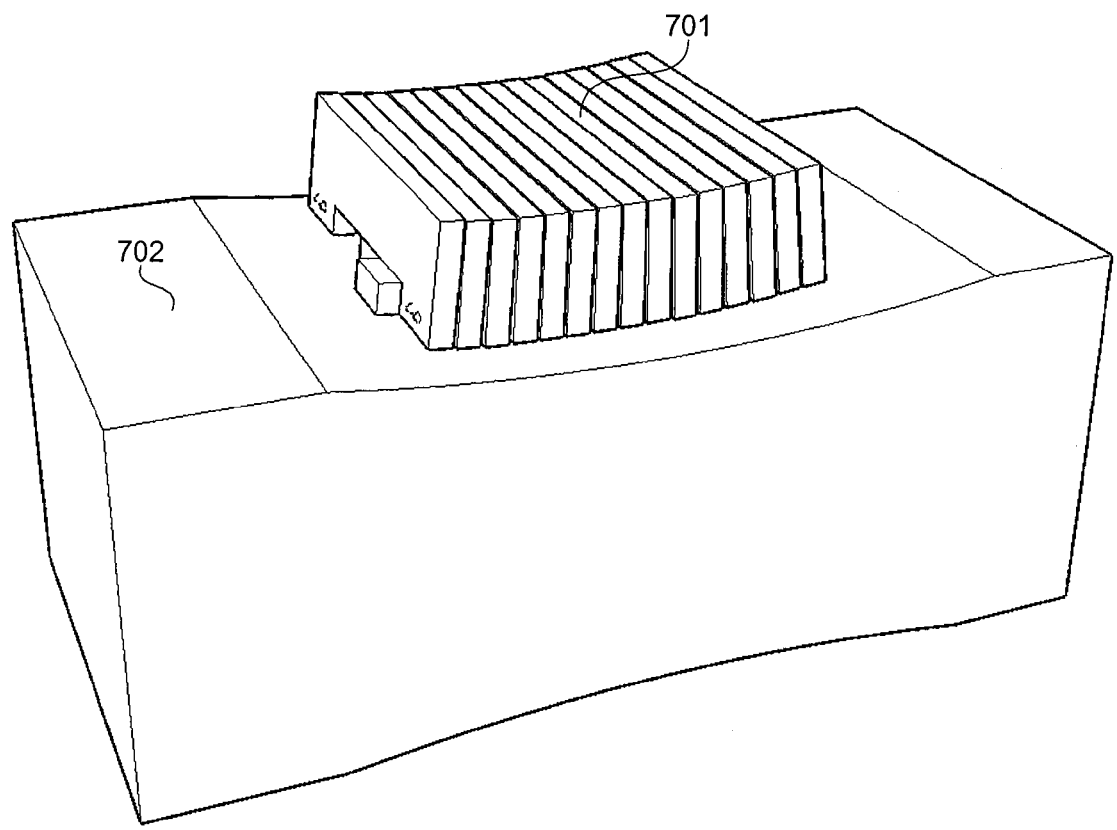
FIG. 7 is a perspective drawing illustrating the flexible array probe of the present disclosure being applied to a concave surface.

FIG. 6 illustrates the flexible array probe of the present disclosure 601 coupled to a convex surface 602. FIG. 7 illustrates the flexible array probe of the present disclosure 701 coupled to a concave surface 702. In both cases, the array probes (601 and 701) have conformed to the geometry of the contoured structure under test (602 and 702) and orientated their elements with a uniform lift off and orthogonal to the surface of the structure under test. With the pivoting mechanisms (the cylindrical tabs 104 and slots 106 of FIGS. 1A and 1B, the spacer balls 204 of FIG. 2, or the chain structure 304 of FIG. 3) in place, each of the probe fins is pulled into correct alignment by those directly adjacent to it, forcing the entire probe structure 601 and 701 to inherently conform to the surface geometry of the structure under test 602 and 702.

It should be noted that while the preferred embodiment of the present disclosure makes use of probe housing elements, the methods of the present disclosure are not limited in this regard. Indeed, the methods of the present disclosure can be used to realize a flexible array probe wherein probe elements are fixed directly to probe fins.

Figure 8:
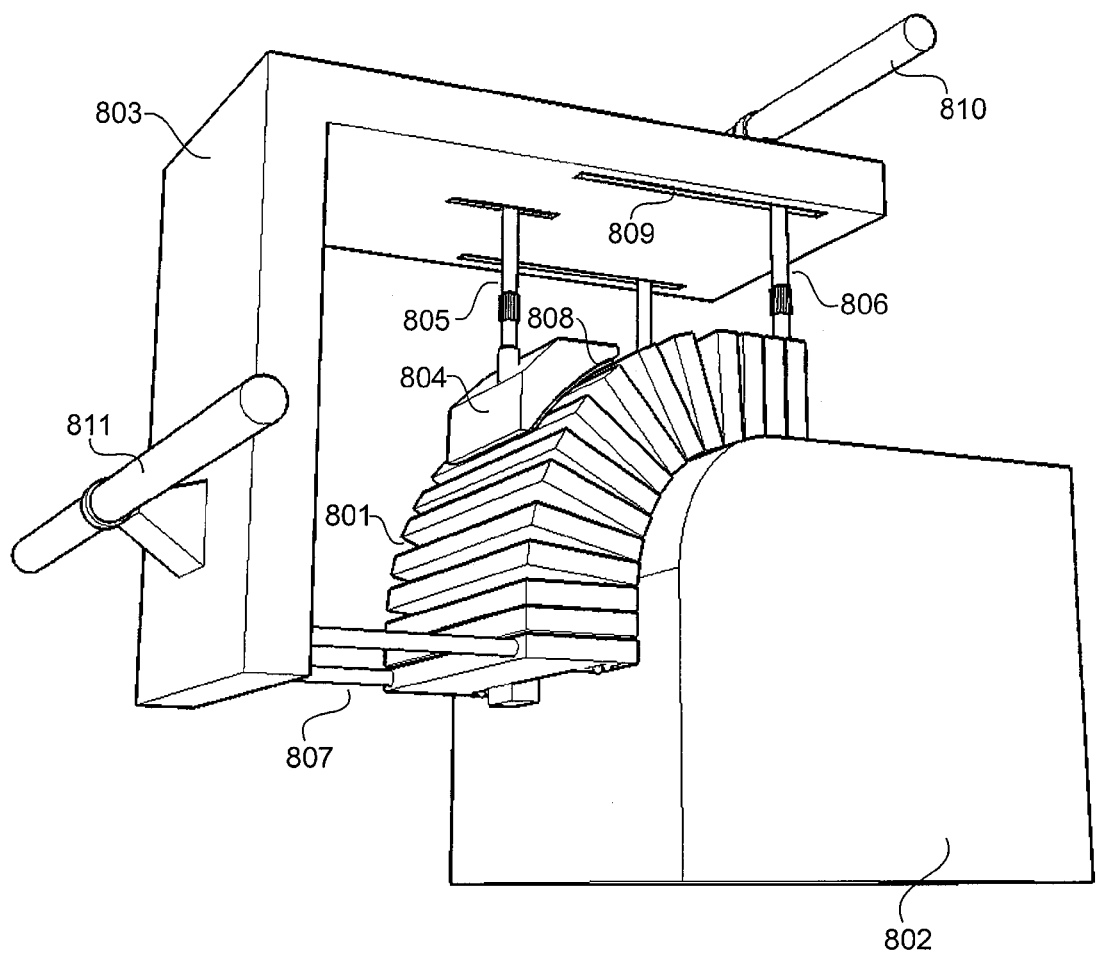
FIG. 8 is a perspective drawing illustrating the flexible array probe of the present disclosure mounted into an alignment and coupling fixture.

FIG. 8 illustrates an alignment and coupling fixture suitable for use with the flexible array probe of the present disclosure. The flexible array probe 801 is coupled to a contoured structure under test 802 by mounting frame 803. Adjustable posts 806 along with fixed posts 807 secure the end points of flexible array probe 801 against the contoured structure under test 802. A pressing mechanism 804—designed to approximate the shape of the structure under test—is mounted on an adjustable post 805 at the critical measurement point. The contact surface 808 of the pressing mechanism 804 can either be made from a hard material—such as, but not limited to, plastic or steel—to provide a ridged contact surface to hold the flexible array probe 801 to a reasonably well-known shape, or an elastomeric material—such as, but not limited to, rubber or silicone—to the flexible array probe 801 to conform to a wider array of test structures.

The alignment posts 806 and 805 are adjustable in two dimensions and can be used to fit the flexible array probe 801 to a wide range of surface sizes and shapes. The pressing mechanism 804 can also be constructed to any shape—such as, but not limited to, a convex or concave curve, a flat wedge, or a complex S-shape—in order to match the structure under test 802 and can be built to any size to allow direct coupling with as many or as few elements of the flexible array probe 801 as required by the application.

Mounting bars 810 and 811 are provided so the entire structure—the probe and the alignment and coupling fixture together—can be mounted into a large automated test system or installed on a production line.

It should be noted that while the alignment and coupling fixture depicted in FIG. 8 makes use of pressing mechanism 804 to accurately couple the flexible array probe 801 against the contoured structure under test 802, the methods of the present disclosure are not limited in this regard. Indeed, within many inspection operations the flexible array probe 801 would be sufficiently coupled to the contoured structure under test 802 by the force applied through alignment posts 806 and 807 alone. Within such an inspection operations, a coupling structure such as pressing mechanism 804 would be unnecessary and therefore not included within the alignment and coupling fixture.

It should also be noted that while the exemplary alignment and coupling fixture depicted in FIG. 8 makes use of an L-shaped mounting frame 803, the methods of the present disclosure are not limited in this regard. While the exemplary mounting frame 803 is well suited for coupling the flexible array probe of the present disclosure to a rounded bar structure—that is, a structure with flat surfaces, each orthogonal with respect to the other, on either side of the curved inspection area—it should be well understood by those skilled in the art that other shaped mounting frames could be employed to effectively couple the flexible array probe of the present disclosure to other types of structures, such as, but not limited to, tubes and rails.

The inventors also contemplate an alignment and coupling fixture wherein alignment posts 805 and 807 are spring loaded within alignment tracks 809, such that the flexible array probe will remain under constant tension as it is applied to a structure under test 802.

Figure 9:
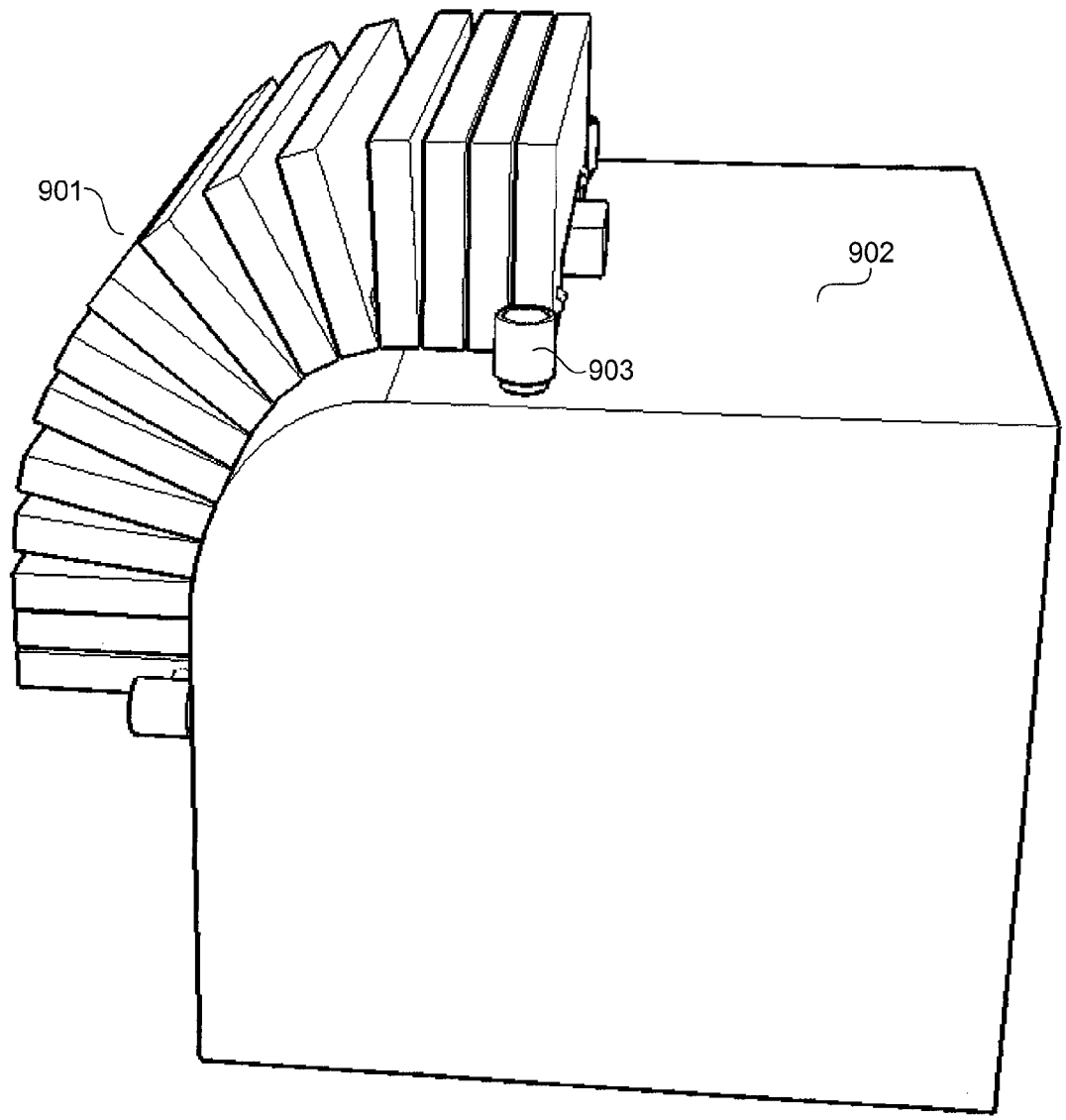
FIG. 9 is a perspective drawing illustrating an alternate embodiment of the flexible array probe of the present disclosure which uses mounted support magnets to couple and align to a structure under test.

FIG. 9 illustrates a simpler method for aligning and coupling the flexible array probe 901 to a ferromagnetic contoured structure under test 902 suitable for spot checking or any otherwise non-automated inspection. A plurality of alignment magnets 903 are mounted onto the individual probe fins and used hold the entire flexible array probe 901 in place. Using an alignment method of this type, the flexible array probe 901 can easily and quickly be moved to different locations on the test piece and adjusted by hand during an inspection. It should be noted that while FIG. 9 shows alignment magnets 903 mounted on only the two outermost probe fins, more alignment magnets 903 may be used depending on the requirements of the application, including an embodiment wherein each probe fin was fixed with its own set of alignment magnets 903.

Figure 10:
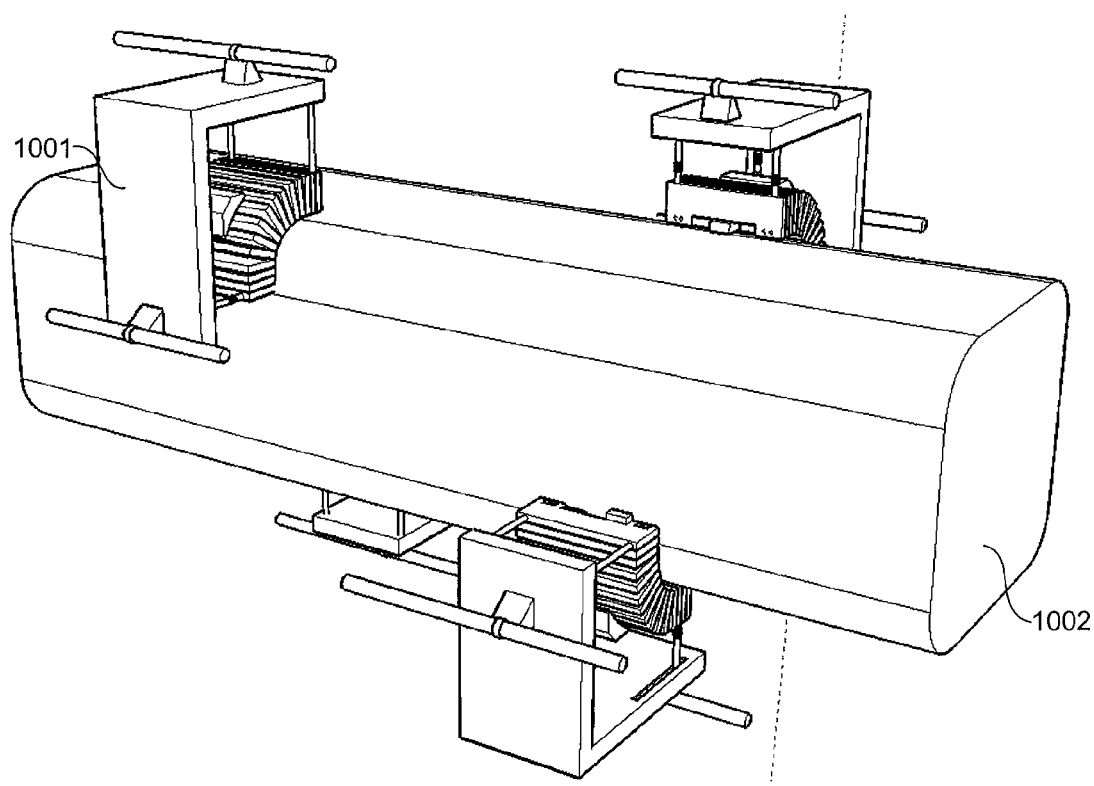
FIG. 10 is a perspective drawing illustrating a plurality of flexible array probes as described by the present disclosure arranged into a large test system.

FIG. 10 illustrates a plurality of flexible array probes 1001 as described by the present disclosure mounted in place around a billet 1002 which has a rounded square cross-section. In this way, the flexible array probe of the present invention can be used as part of a large test system to provide full coverage of a complex part.

Figure 11:
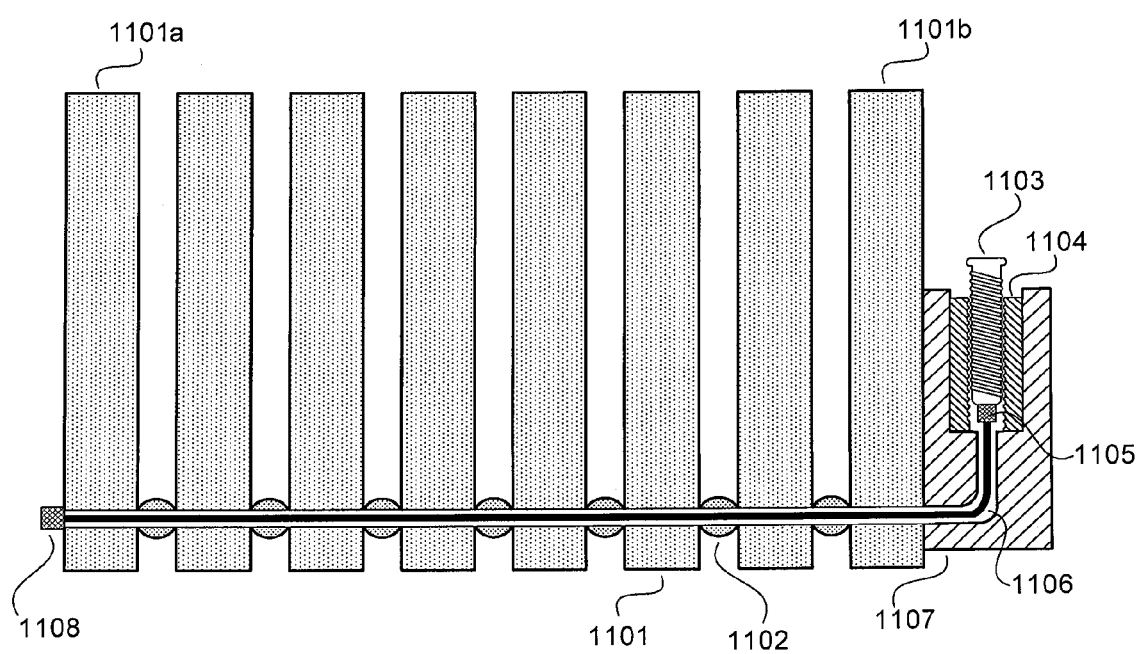
FIG. 11 is a cutaway assembly drawing illustrating an alternate embodiment of the flexible array probe of the present disclosure wherein the degree of flexibility within the probe can be adjusted after assembly.

FIG. 11 is a cutaway assembly drawing depicting an alternate embodiment of the flexible array probe of the present disclosure wherein the tension of the one or more wires 1106 coupling the probe fins 1101 to each other can be adjusted after assembly. In this way, life cycle changes in wire tension, which can be detrimental the an inspection operation's effectiveness and accuracy, can be easily corrected without disassembly of the probe.

A first wire securement element 1108 fixes a first end of wire 1106 to the first probe fin 1101b. The wire 1106 is then drawn through each of the probe fins 1101 and spacer elements 1102, and a second wire securement element 1105 fixes a second end of wire 1106 to the end of a tension adjustment screw 1103. The tension adjustment screw 1103 is secured within a threaded slot 1104 within housing element 1107. Housing element 1107 is then further secured against the last probe fin 101a. By manipulating the tension adjustment screw 1103 within the threaded slot 1104 the tension of the wire 1106 can be adjusted, providing an operator means to maintain flexibility of the flexible array probe of the present disclosure as is optimal for a given inspection operation.

As previously mentioned in the discussion of FIG. 5, the securement elements 1105 and 1008 can take a plurality of forms dependant on the needs of the inspection operation. Such forms include, but are not limited to, epoxy, clamps, clips, mounting screws, and stop sleeves. Further, while the cutaway assembly drawing depicted in FIG. 11 shows a single wire 1106 and a single tension adjustment screw 1104 for ease of explanation, the methods of the present disclosure are not limited in this regard. Indeed, a plurality of such wires and adjustment elements would likely be used in most flexible array probe assemblies.

It should also be noted that while the exemplary probe in FIG. 11 depicts the tension screw housing element 1107 as a separate element affixed to probe fin 1101b, the methods of the present disclosure are not limited in this regard. Indeed, in many practical applications of the methods of the present disclosure, such a housing element would be integrated into probe fin 1101b.

Figure 12:
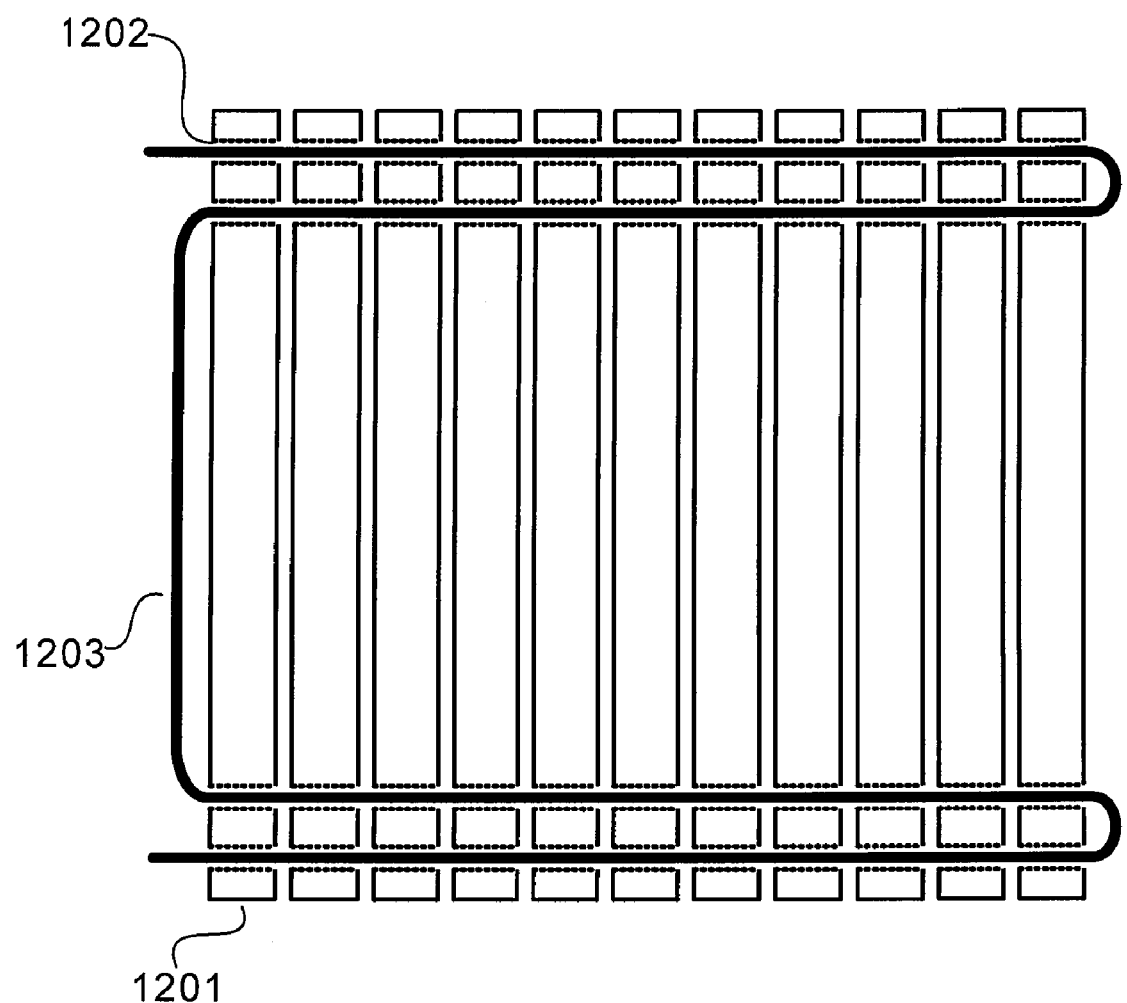
FIG. 12 is a cutaway assembly drawing illustrating a single wire assembly method for the flexible array probe of the present disclosure.

FIG. 12 is a cutaway assembly drawing illustrating a single wire assembly technique for a flexible array probe built according to the methods of the present disclosure. A single long wire 1203 is drawn through a plurality of probe fins 1201 via multiple holes 1202 in each probe fin 1201. Said long wire 1203 is treaded through each probe fin multiple times such as to effectively draw the plurality of probe fins together.

Although the present invention has been described in relation to particular embodiments thereof, many other variations and modifications and other uses will become apparent to those skilled in the art. It is preferred, therefore, that the present invention not be limited by the specific disclosure herein.

What is claimed:

1. A flexible array probe for use with a non-destructive inspection operation, said probe comprising:
a plurality of probe fins, said plurality comprising a first probe fin and a last probe fin;
a plurality of probe elements, each probe element fixed to one of the plurality of probe fins;
a plurality of pivot mechanisms, a respective at least one of the pivot mechanisms being situated between respective, adjacent surfaces of the probe fins;
at least one wire element having a first end and a second end, said wire elements drawn through the plurality of probe fins;
at least one first securement element affixing the first end of each wire element to at least one of the probe fins; and
at least one second securement element affixing the second end of each wire element to at least one of the probe fins.

2. The flexible array probe of claim 1, wherein at least one hole is made through each probe fin allowing wire elements to be drawn through said probe fins.

3. The flexible array probe of claim 1, wherein the wire elements are also drawn through the plurality of pivot mechanisms.

4. The flexible array probe of claim 3, wherein at least one hole is made through each pivot mechanism allowing wire elements to be drawn through said pivot mechanisms.

5. The flexible array probe of claim 1, wherein the pivot mechanisms are spacer elements.

6. The flexible array probe of claim 5, wherein the spacer elements are made from a group of materials consisting of copper, plastic, rubber, carbide, bronze, Polyetheretherketone, and Acetal.

7. The flexible array probe of claim 5, wherein the spacer elements are made from a self lubricating material.

8. The flexible array probe of claim 5, wherein spacer element alignment slots are provided on the probe fins.

9. The flexible array probe of claim 1, wherein the pivot mechanisms are shaped tabs and slots molded onto the plurality of probe fins.

10. The flexible array probe of claim 1, wherein the pivot mechanisms are shaped tabs and slots machined into the plurality of probe fins.

11. The flexible array probe of claim 1, wherein at least one of the securement elements includes a means to adjust the tension in at least one of the wire elements.

12. The flexible array probe of claim 11, wherein the means for tension adjustment comprises a tension adjustment screw secured to at least one of the wire elements.

13. The flexible array probe of claim 1, in which the probe elements are fixed within probe housings.

14. The flexible array probe of claim 1, wherein the probe elements are eddy current sensors.

15. The flexible array probe of claim 1, wherein the probe elements are piezoelectric sensor elements.

16. The flexible array probe of claim 1, wherein the probe elements are magnetic flux leakage sensors.

17. The flexible array probe of claim 1, further comprising wear elements fixed to at least one surface of the probe fins.

18. The flexible array probe of claim 1, further comprising an alignment and coupling structure, said structure comprising a frame element and a plurality of alignment posts fixed to at least one of the probe fins.

19. The flexible array probe of claim 18, wherein at least one of the alignment posts is adjustable in length.

20. The flexible array probe of claim 18, wherein at least one of the alignment posts is spring loaded as to maintain constant tension on said flexible array probe.

21. The flexible array probe of claim 18, further comprising a pressing mechanism for providing coupling force to least one of the probe fins.

22. The flexible array probe of claim 21, wherein the pressing mechanism takes a geometric shape corresponding to a curved surface under test.

23. The flexible array probe of claim 1, further comprising an alignment and coupling structure, said structure comprising a plurality of support posts extending from at least one of the probe fins and at least one alignment magnet fixed to at least one of said support posts.

24. A flexible array probe for use with a non-destructive inspection operation, said probe comprising:
   a plurality of probe fins, said plurality comprising a first probe fin and a last probe fin;
   a plurality of probe elements, each probe element fixed to one of the plurality of probe fins;
   a plurality of rigid link elements, corresponding ones of said rigid link elements being affixed to respective ones of the plurality of probe fins, said link elements coupled together to form at least one chain assembly and adjacent ones of said link elements being attached by a respective pivot joint.

25. The flexible array probe of claim 24, wherein the individual link elements are secured in such a way as to be unable to rotate with respect to the probe fin to which each individual link element is attached.

26. The flexible array probe of claim 24, wherein the chain assemblies are rigid, such that the array probe will tend to hold its shape when positioned.

27. The flexible array probe of claim 24, in which the probe elements are fixed within probe housings.

28. The flexible array probe of claim 24, wherein the probe elements are eddy current sensors.

29. The flexible array probe of claim 24, wherein the probe elements are piezoelectric sensor elements.

30. The flexible array probe of claim 24, wherein the probe elements are magnetic flux leakage sensors.

31. The flexible array probe of claim 24, further comprising wear elements fixed to at least one surface of the probe fins.

32. The flexible array probe of claim 24, further comprising an alignment and coupling structure, said structure comprising a frame element and a plurality of alignment posts fixed to at least one of the probe fins.

33. The flexible array probe of claim 32, wherein at least one of the alignment posts is adjustable in length.

34. The flexible array probe of claim 32, wherein at least one of the alignment posts is spring loaded as to maintain constant tension on said flexible array probe.

35. The flexible array probe of claim 32, further comprising a pressing mechanism for providing coupling force to least one of the probe fins.

36. The flexible array probe of claim 35, wherein the pressing mechanism takes a geometric shape corresponding to a curved surface under test.

37. The flexible array probe of claim 24, further comprising an alignment and coupling structure, said structure comprising a plurality of support posts extending from at least one of the probe fins and at least one alignment magnet fixed to at least one of said support posts.

* * * * *